United States Patent [19]

Tanida et al.

[11] 4,153,629

[45] May 8, 1979

[54] 9,10-DIHYDRO-9,10-METHANOANTHRACENE N-OXIDE

[75] Inventors: Hiroshi Tanida, Osaka; Tadashi Irie, Suita, both of Japan

[73] Assignee: Shionogi & Co., Ltd., Osaka, Japan

[21] Appl. No.: 750,630

[22] Filed: Dec. 15, 1976

[30] Foreign Application Priority Data

Dec. 15, 1975 [GB] United Kingdom ............... 51318/75

[51] Int. Cl.² .................................................. C07C 87/28
[52] U.S. Cl. ......................... 260/570.8 TC; 260/501.1;
260/501.21; 260/544 B; 260/558 R; 260/567.5;
424/250; 424/267; 424/316; 424/330; 544/380;
562/492; 546/195
[58] Field of Search .................. 260/570.8 TC, 501.21,
260/501.1

[56] References Cited

U.S. PATENT DOCUMENTS

| | | | |
|---|---|---|---|
| 3,299,139 | 1/1967 | Pedersen ........................... | 260/570.8 |
| 3,399,201 | 8/1968 | Schmidt et al. ................... | 260/570.8 X |
| 3,493,616 | 2/1970 | Symon .............................. | 260/570.8 X |
| 3,579,582 | 5/1971 | Symon .............................. | 260/574 |
| 3,622,630 | 11/1971 | Craig et al. ....................... | 260/570.8 |
| 3,952,017 | 4/1976 | Kyburz et al. ................... | 260/570.8 X |

FOREIGN PATENT DOCUMENTS

618034  2/1949  United Kingdom .................. 260/570.8

*Primary Examiner*—Robert V. Hines
*Attorney, Agent, or Firm*—Birch, Stewart, Kolasch and Birch

[57] ABSTRACT

9,10-Dihydro-9,10-methanoanthracene N-oxide derivatives represented by the formula:

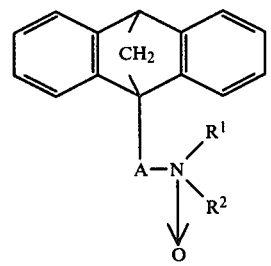

wherein A represents a straight or branched $C_1$-$C_6$ alkylene; $R^1$ and $R^2$ each represents $C_1$-$C_4$ alkyl or phenyl-$C_1$-$C_4$ alkyl, or

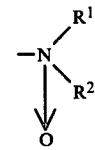

represents the group

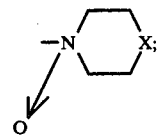

and X represents methylene, hydroxymethylene, $C_1$-$C_4$

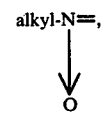

or hydroxy-$C_1$-$C_4$

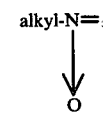

and their pharmaceutically acceptable acid addition salts which are useful as anti-depressants, tranquilizers, or anti-epileptics.

1 Claim, No Drawings

9,10-DIHYDRO-9,10-METHANOANTHRACENE N-OXIDE

The present invention relates to 9,10-dihydro-9,10-methanoanthracene N-oxide derivatives and to the production thereof. More particularly, this invention relates to 9,10-dihydro-9,10-methanoanthracene N-oxide derivatives represented by the formula:

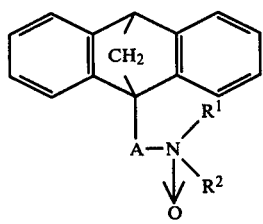 (I)

wherein A represents a straight or branched $C_1$-$C_6$ alkylene; $R^1$ and $R^2$ each represents $C_1$-$C_4$ alkyl or phenyl-$C_1$-$C_4$ alkyl, or 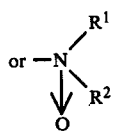

represents the group

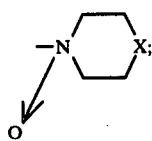

and X represents methylene, hydroxymethylene, $C_1$-$C_4$

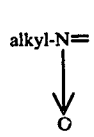

or hydroxy-$C_1$-$C_4$

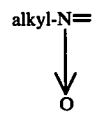

and their acid addition salts, which are useful as antidepressants, tranquilizers, or anti-epileptics. Furthermore, it relates to the production the above compounds (I).

In the above definition, the straight or branched $C_1$-$C_6$ alkylene involves methylene, ethylene, propylene, trimethylene, tetramethylene, 2-methyl-tetramethylene, 2-ethyltetramethylene, pentamethylene, and hexamethylene. The $C_1$-$C_4$ alkyl includes methyl, ethyl, propyl, isopropyl, butyl, isobutyl, and t-butyl.

The preferred significance for A is $C_3$-$C_4$ alkylene. The preferred significance for each $R^1$ and $R^2$ is $C_1$-$C_3$ alkyl, especially methyl.

The compounds represented by the formula (I) may form pharmaceutically acceptable salts with a variety of inorganic or organic acids. Such salts include the hydrochloride, sulfate, nitrate, phosphate, thiocyanate, acetate, succinate, oxalate, maleate, malate, phthalate, methanesufonate, and salicylate.

The objective compounds of this invention can be prepared by several methods, one of which is shown by the following scheme:

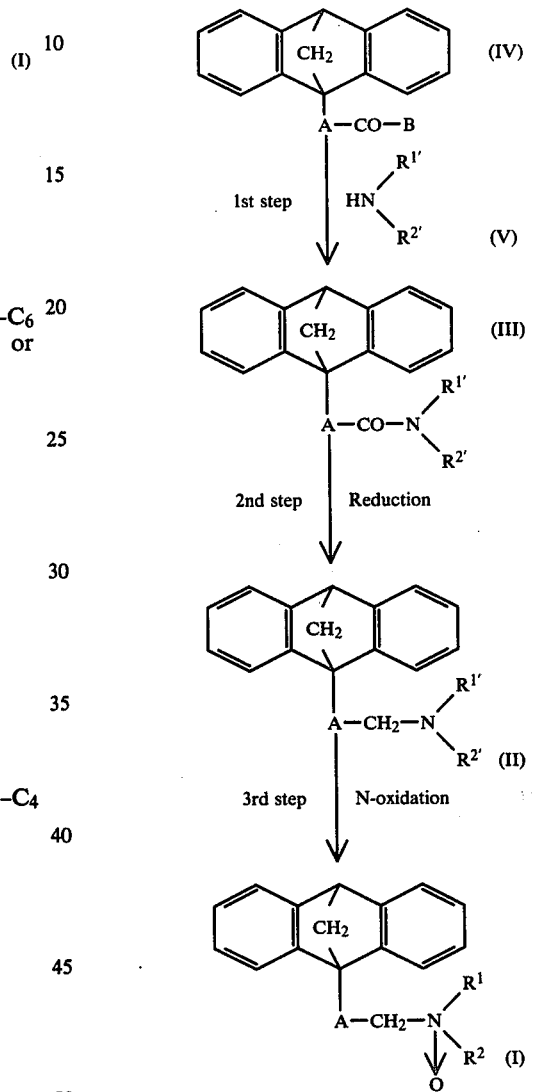

wherein B represents a reactive group (e.g. halogen, a residue of ester); $R^{1'}$ and $R^{2'}$ each represents $C_1$-$C_4$ alkyl or phenyl-$C_1$-$C_4$ alkyl, or

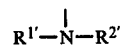

represents the group

$X'$ represents methylene, hydroxymethylene, $C_1$-$C_4$ alkyl-N= or hydroxy-$C_1$-$C_4$ alkyl-N=; and A, $R^1$ and $R^2$ each is as defined above.

The starting compound (IV), for example, 9,10-dihydro-9,10-methano-9-anthrylcarbonyl chloride (IVa) is prepared by using benzonorbornadiene-1-carboxylic acid (VI) [Chenier et al., J. Org. Chem., 38, 4350 (1973)] as in the following scheme:

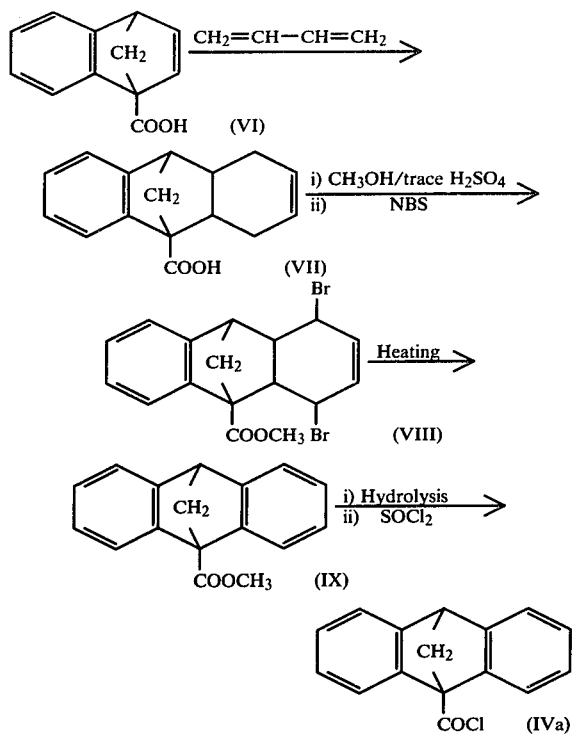

Other starting compounds, for example, 9,10-dihydro-9,10-methano-9-anthrylacetyl chloride can be prepared by subjecting 9,10-dihydro-9,10-methano-9-anthrylcarbonyl chloride (IVa) to a conventional procedure for increasing the carbon chain such as the Arndt-Eistert reaction.

The first step of this invention is carried out by reacting the starting compound (IV) with the compound (V), if necessary, in an excess amount in a solvent (e.g. chloroform, methylene chloride, dimethylformamide, dioxane) at room temperature or under cooling. Examples of the compound (V) are dimethylamine, diethylamine, methylethylamine, methylbenzylamine, piperidine, 4-hydroxypiperidine, N-methylpiperazine, and N-(2-hydroxyethyl)piperazine.

The second step of the process is carried out by reducing the amide (III) with a metallic hydride complex such as lithium aluminum hydride or potassium aluminum hydride in an inert solvent (e.g. tetrahydrofuran, dioxane, ether) with warming.

Thus-obtained amine derivative (II) is subjected to N-oxidation in the third step. The third step is carried out by treating the amine (II) with an N-oxidizing agent (e.g. hydrogen peroxide, perphthalic acid, peracetic acid) in a suitable solvent (e.g. methanol, acetic acid, acetone, chloroform, dimethylformamide) at room temperature or under cooling or heating.

The 9,10-dihydro-9,10-methanoanthracene N-oxide derivatives may be converted into pharmaceutically acceptable acid addition salts as mentioned above.

The 9,10-dihydro-9,10-methanoanthracene N-oxide derivatives (I) and their acid addition salts are useful as anti-depressants, tranquilizers, and anti-epileptics. The pharmacological test examined by the following methods shows that 9-(3-dimethylaminopropyl)-9,10-dihydyro-9,10-methanoanthracene N-oxide is as potent in antagonism to reserpine ptosis as imipramine, a commercially available anti-depressant, but about 4 times less toxic in the acute toxicity than the drug.

Test Method

Anti-reserpine ptosis: This test was effected on a group of 10 female Wistar rats, their body weight ranging from 200 to 230 g. A prescribed amount of the test compound was orally administered, and 30 minutes later reserpine (5 mg/kg) was intraperitoneally administered. After the lapse of 4 hours, the effect of the test compound on the reserpine-induced ptotic symptom was observed in 9 orders. [Rubin et al., J. Pharmacol. exp. Therap., 120, 125 (1957)]. Acute toxicity: The test compound was orally administered to DS male mice in different single doses. For each dose, 10 mice were used, their body weight ranging from 20 to 23 g. The mice were observed for 72 hours after the administration of the compound. The mortality was calculated by the Bliss method [Bliss, Ann. Appl. Biol., 22, 134–307 (1935); Quant, J. Pharmacol., 11, 192 (1938)].

Other compounds of this invention exhibit similar pharmacological activities.

Thus, the compounds (I) and their pharmaceutically acceptable acid addition salts are useful in the treatment of, for example, manic-depressive insanity and epilepsy.

The 9,10-dihydro-9,10-methanoanthracene N-oxide derivatives (I) or their pharmaceutically acceptable acid addition salts are applicable singly or in combination with pharmaceutically suitable carriers such as wheat starch, corn starch, potato starch, gelatin, and the like. The choice of carriers is determined by the preferred route of administration, the solubility of the substance and the standard pharmaceutical practice. Examples of pharmaceutical preparations are tablets, capsules, pills, suspensions, syrups, powders, and solutions. These compositions can be prepared in a conventional manner. A suitable dosage of the 9,10-dihyro-9,10-methanoanthracene N-oxide derivatives (I) or their pharmaceutically acceptable acid addition salts for human adults is in the order of about 10 to 200 mg per day.

Presently preferred and practical embodiments of the present invention are illustratively shown in the following examples.

EXAMPLE 1

(1) 9,10-Dihydro-9,10-methano-9-anthrylpropionic acid (585 mg) is treated with thionyl chloride to give 9,10-dihydro-9,10-methano-9-anthrylpropionyl chloride. To a solution of the obtained chloride in methylene chloride is added a solution of dimethylamine in methylene chloride under ice cooling. The resultant reaction mixture is washed with dilute hydrochloric acid and water in order, dried, and evaporated to give N,N-dimethyl-9,10-dihdyro-9,10-methanoanthrylpropionamide (580 mg). The product is recrystallized from a mixture of methylene chloride and hexane to give crystals melting at 179° to 180.5° C.

NMR (in CDCl$_3$) δ 2.4 (d, 2H), 2.61 (m, 4H), 2.85 (s, 3H), 2.90 (s, 3H), 4.25 (s, 1H), 6.8–7.4 (m, 8H).

IR (in CHCl$_3$) 1640 cm$^{-1}$

Anal. Calcd. for C$_{20}$H$_{21}$ON: C, 82.44; H, 7.26; N, 4.81. Found: C, 82.34; H, 7.16; N, 5.07.

(2) The above product, N,N-dimethyl-9,10-dihydro-9,10-methanoanthrylpropionamide (560 mg) is reduced with lithium aluminum hydride in tetrahydrofuran to give 9-(3-dimethylaminopropyl)-9,10-dihydro-9,10-methanoanthracene, which is treated with hydrogen chloride in ether to yield a white precipitate. The precipitate is obtained by filtration. Rescrystallization from a mixture of methanol and ether gives 9-(3-dimethylaminopropyl)-9,10-dihydro-9,10-methanoanthracene hydrochloride melting above 230° C.

Anal. Calcd. for $C_{20}H_{24}NCl$; C, 76.53; H, 7.71; N, 4.46; Cl, 11.30. Found: C, 76.28; H, 7.54; N, 4.57; Cl, 11.44.

(3) The free base of the product obtained above, 9-(3-dimethylaminopropyl)-9,10-dihydro-9,10-methanoanthracene (964 mg), is dissolved in methanol (3 ml). To the solution is added a solution of 30% hydrogen peroxide (395 mg) in methanol (3 ml) under ice cooling and stirring, and the resultant mixture is allowed to stand at room temperature for 2 days. The reaction mixture is evaporated under reduced pressure, and the residue is crystallized from benzene to give 9-(3-dimethylaminopropyl)-9,10-dihydro-9,10-methanoanthracene N-oxide (950 mg). The substance is recrystallized from a mixture of methylene chloride and hexane to give crystals melting at 147° C. (decomp.).

NMR (in $CDCl_3$) δ 2.3 (m, 4H), 2.4 (broad s, 2H), 3.1 (s, 6H), 3.3 (m, 2H), 4.2 (s, 1H), 6.8–7.3 (m, 8H).

Anal. Calcd. for $C_{20}H_{23}ON.1.4H_2O$: C, 75.39; H, 8.16; N, 4.40. Found: C, 75.40; H, 7.88; N, 4.68.

EXAMPLES 2–7

The following compounds are prepared by procedures similar to those in Example 1.

| Ex. No. | A | II $R^{1'}$—N—$R^{2'}$ mp(°C.) | I $R^1$—N(→O)—$R^2$ mp(°C.) |
|---|---|---|---|
| 2 | —(CH$_2$)$_3$— | —N⟨piperidine⟩—OH  168–169 | —N(→O)⟨piperidine⟩—OH  158–159(d)** |
| 3 | —(CH$_2$)$_3$— | —N⟨piperazine⟩N—CH$_2$CH$_2$OH  153.5–154.5 | —N(→O)⟨piperazine⟩N(→O)—CH$_2$CH$_2$OH  153–157(d) |
| 4 | —(CH$_2$)$_3$— | —N⟨piperazine⟩N—CH$_3$  121–122  >230* | —N(→O)⟨piperazine⟩N(→O)—CH$_3$  203(d)** |
| 5 | —CH$_2$CH(CH$_3$)CH$_2$— | —N(CH$_3$)$_2$  >230* | —N(→O)(CH$_3$)$_2$  113–114 (d) |
| 6 | —(CH$_2$)$_3$— | —N(CH$_3$)(C$_2$H$_5$)  Oil | —N(→O)(CH$_3$)(C$_2$H$_5$)  159.5–160.5** |

-continued
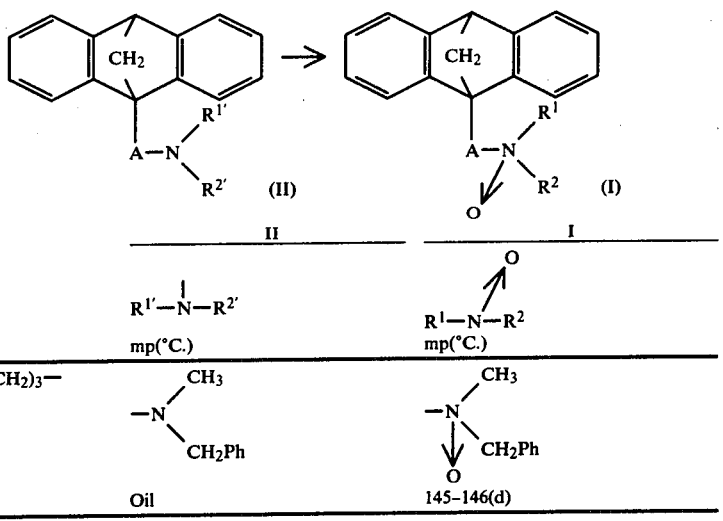
| Ex. No. | A | $R^{1'}-\overset{|}{N}-R^{2'}$ mp(°C.) | $R^1-N-R^2$ with →O mp(°C.) |
|---|---|---|---|
| 7 | —(CH$_2$)$_3$— | —N(CH$_3$)(CH$_2$Ph) Oil | —N(CH$_3$)(CH$_2$Ph)→O 145–146(d) |
Note:
*Hydrochloride
(d)Decomposition
**Picrate
What is claimed is:
1. The compound 9-(3-dimethylaminopropyl)-9,10-dihydro-9,10-methanoanthracene N-oxide.
* * * * *